(12) United States Patent
Wessman et al.

(10) Patent No.: US 9,534,011 B2
(45) Date of Patent: Jan. 3, 2017

(54) APPARATUS AND METHOD FOR SOLID PHASE SYNTHESIS

(71) Applicant: Biotage AB, Uppsala (SE)

(72) Inventors: Anders Wessman, Vange (SE); Axel Strandell, Uppsala (SE)

(73) Assignee: BIOTAGE AB, Uppsala (SE)

( * ) Notice: Subject to any disclaimer, the term of this patent is extended or adjusted under 35 U.S.C. 154(b) by 0 days.

(21) Appl. No.: 14/424,814

(22) PCT Filed: Sep. 2, 2013

(86) PCT No.: PCT/EP2013/068097
§ 371 (c)(1),
(2) Date: Feb. 27, 2015

(87) PCT Pub. No.: WO2014/033297
PCT Pub. Date: Mar. 6, 2014

(65) Prior Publication Data
US 2015/0225444 A1   Aug. 13, 2015

Related U.S. Application Data

(60) Provisional application No. 61/695,536, filed on Aug. 31, 2012.

(30) Foreign Application Priority Data

Aug. 31, 2012 (EP) ..................... 12182642

(51) Int. Cl.
| | |
|---|---|
| *B01J 19/00* | (2006.01) |
| *C07K 1/04* | (2006.01) |
| *B01F 11/00* | (2006.01) |
| *B01J 19/12* | (2006.01) |
| *B01J 19/28* | (2006.01) |
| *B01J 8/10* | (2006.01) |

(52) U.S. Cl.
CPC ............ *C07K 1/045* (2013.01); *B01F 11/0002* (2013.01); *B01J 8/10* (2013.01); *B01J 19/0046* (2013.01); *B01J 19/126* (2013.01); *B01J 19/28* (2013.01); *B01J 2208/00442* (2013.01); *B01J 2208/00858* (2013.01); *B01J 2219/005* (2013.01); *B01J 2219/00141* (2013.01); *B01J 2219/00286* (2013.01); *B01J 2219/00423* (2013.01); *B01J 2219/00495* (2013.01); *B01J 2219/00596* (2013.01); *B01J 2219/00725* (2013.01)

(58) Field of Classification Search
CPC ................................. B01J 8/382; B01J 37/08
USPC ............................... 422/186.29, 129; 436/21
See application file for complete search history.

(56) References Cited

U.S. PATENT DOCUMENTS

| | | | |
|---|---|---|---|
| 5,858,178 A * | 1/1999 | Lautenschlager | .......... B01J 3/04 159/22 |
| 6,084,226 A * | 7/2000 | Greene | .................. B01J 19/126 219/710 |
| 2004/0188354 A1* | 9/2004 | Jamalabadi | ............ B01D 15/16 210/656 |

* cited by examiner

*Primary Examiner* — Natalia Levkovich
(74) *Attorney, Agent, or Firm* — Harness, Dickey & Pierce, PLC

(57) ABSTRACT

An apparatus for microwave assisted solid phase synthesis using solid-phase resin beads mixed with a liquid solvent comprising a generally cylindrical reactor made of microwave transparent material and having a central axis, the reactor having an inlet and an outlet; a porous frit associated with the outlet of the reactor, the porous frit preventing discharge of beads and allowing discharge of the solvent from the reactor; and means for concentric rotation of the reactor around the central axis in alternating clockwise and anti-clockwise directions. A method for microwave assisted solid phase synthesis using the apparatus is also disclosed.

9 Claims, 1 Drawing Sheet

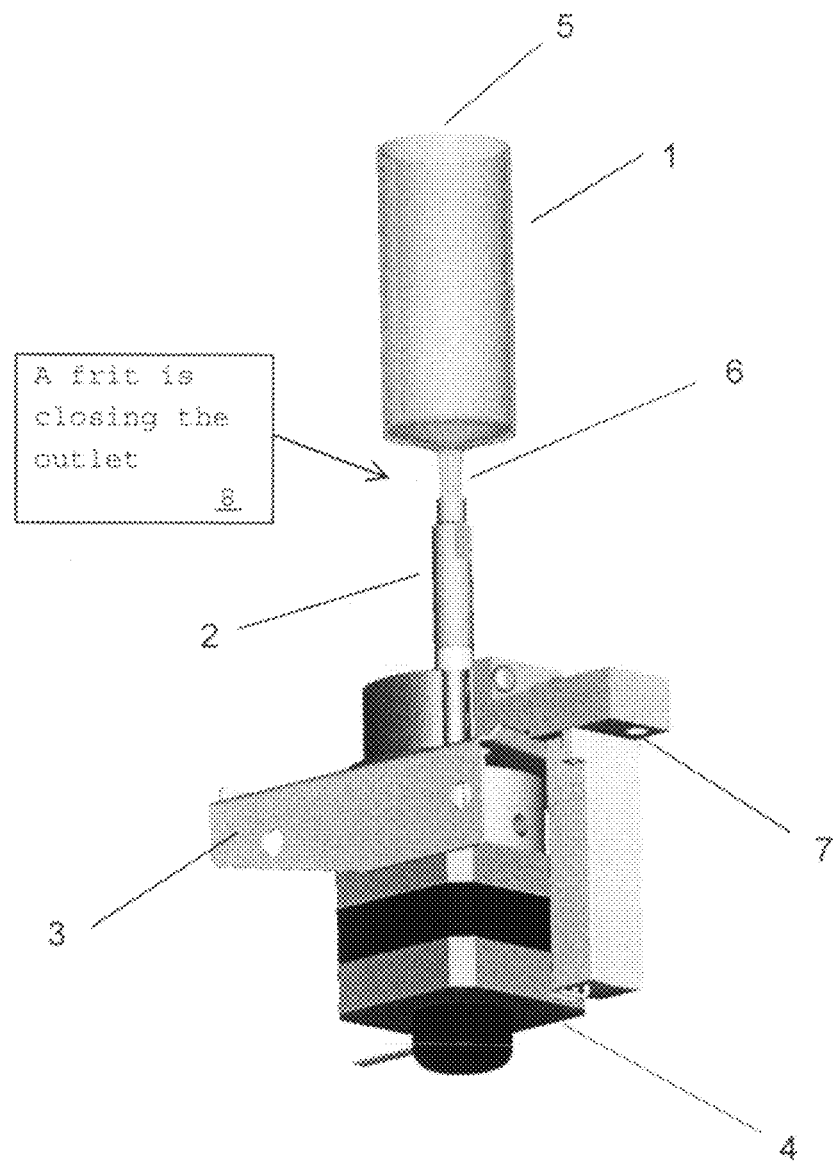

APPARATUS AND METHOD FOR SOLID PHASE SYNTHESIS

CROSS-REFERENCE TO RELATED APPLICATIONS

This application is a National Phase under 35 U.S.C. §371 of PCT International Application Number PCT/EP2013/068097, filed Sep. 2, 2013, which claims priority under 35 U.S.C. §119 to European Patent Application Number EP 12182642.4, filed on Aug. 31, 2012 and benefit to U.S. Provisional Application No. 61/695,536, filed on Aug. 31, 2012, the entire contents of which are hereby incorporated by reference.

FIELD OF THE INVENTION

The present invention relates to solid phase synthesis, and more particularly to an apparatus and method for microwave-assisted solid phase synthesis with improved mixing.

BACKGROUND OF THE INVENTION

Solid-phase peptide synthesis (SPPS) is now the accepted method for creating peptides and proteins in the laboratory in a synthetic manner. Small porous solid beads (typically resin) are treated with functional units, or linkers, on which peptide chains can be built. The peptide will remain covalently attached to the bead until cleaved from it by a reagent, such as trifluoroacetic acid.

The general principle of solid-phase peptide synthesis involves repeated cycles of coupling, wash, deprotection, and wash steps (Chan and White, "Fmoc solid phase peptide synthesis: A practical approach", Oxford University Press, Oxford, England, 2000). The free N-terminal amine of a solid-phase attached peptide is coupled to a single N-protected amino acid unit. The formed unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble beads.

The use of microwave irradiation in peptide synthesis has reduced coupling reaction times substantially, and also permitted preparation of long peptide sequences with high degrees of yield and low degrees of racemization (Pedersen, S. L., et al. Microwave heating in solid-phase peptide synthesis. *Chem. Soc. Rev.* 2012, 41, 1826-1844).

In solid phase synthesis, the mass transfer around the resin beads is of great importance. To achieve this, different kinds of mixing techniques are used in today's solid phase peptide synthesis instruments, including, for instance, vortex mixers (sometimes described as variable oscillating mixers), $N_2$ bubbling, recirculation, and inversion mixers.

In a microwave based instrument for peptide synthesis, the microwave cavity of the instrument has a limited volume which determines the maximum size of the reaction vial, the filling degree of which is in turn determined by the mixing technique used.

Since using a magnetic stirrer, a paddle or some other mechanical device for mixing might damage the peptide synthesis resin beads, vortex mixing has typically been used in commercial instruments.

WO 99/56863 discloses a mixing device for mixing liquids and/or solids wherein a container, typically a cylindrical vessel, which is received in a holder can be rotated alternately in clockwise and anti-clockwise direction about the axis of the container by means of a drive mechanism. The angular displacement of the container is regulated by a control unit. In addition to providing for efficient mixing, the device enables the meniscus deflection to be kept small such that mixing is also possible in almost completely filled vessels without a closure.

SUMMARY OF THE INVENTION

With a vortex mixer, the vial for the resin beads is caused to oscillate rapidly in a circular motion which requires a space that is much wider than the diameter of the vial and also a vial that is much higher than the height of the reagent/resin solvent mix in rest. The maximum resin/liquid volume that can be heated and mixed in a given microwave cavity is therefore substantially reduced.

It is an object of the present invention to provide for improved microwave assisted solid phase synthesis through mixing by alternating clockwise and anti-clockwise rotation to thereby permit the use of larger reaction vials and greater volumes therein that can be heated than with vortex mixing according to the prior art.

The above and other objects are achieved by an apparatus for microwave assisted solid phase synthesis using solid-phase resin beads mixed with a liquid solvent, comprising:
  a generally cylindrical reactor made of microwave transparent material and having a central axis, the reactor having an inlet and an outlet;
  a porous frit associated with the outlet of the reactor, the porous frit preventing discharge of beads and allowing discharge of the solvent from the reactor; and
  means for concentric rotation of the reactor around the central axis in alternating clockwise and anti-clockwise directions.

In another aspect, the present invention relates to a method for microwave assisted solid phase synthesis, comprising the steps of:
  providing an apparatus as defined above, wherein the reactor contains functionalized resin beads, solvent and reactant;
  subjecting the reactor to microwave heating while simultaneously mixing by the contents of the reactor by rotating the reactor around the central axis in alternating directions.

Since the reactor is only rotated around its central axis and not shaken as if it would have been if it had been vortexed, the reactor can have a diameter almost as large as the microwave cavity. Further, by only spinning the vial and not vortexing it, the surface turbulence is much less which makes it possible to utilize the height of the reactor more effectively, i.e. a greater fraction of the vial volume can be filled than when using a vortexing mixer.

Preferred embodiments of the above apparatus and method aspects of the invention are set forth in the dependent claims.

In the following, the invention will be described in more detail, by way of example only, with regard to a non-limiting embodiment thereof, reference being made to the accompanying drawing.

BRIEF DESCRIPTION OF THE APPENDED DRAWING

FIG. 1 is a perspective view of an embodiment of the apparatus for microwave-assisted solid phase synthesis according to the present invention.

DETAILED DESCRIPTION OF THE INVENTION

As mentioned above, the present invention relates to an apparatus for microwave assisted solid phase synthesis, such as peptide synthesis, oligonucleotide synthesis or other organic synthesis.

FIG. 1 shows an embodiment of the apparatus which is a part of a system microwave-assisted solid phase synthesis, the rest of the system not being shown in the FIGURE. Referring to FIG. 1, a reactor vial 1, to be filled with resin beads and solvent liquid, is mounted to a rotatable tubular shaft 2 supported by a support 3 and connected to a mixer motor 4. The reactor vial 1, which is made of a microwave-transparent material, e.g. polypropene (PP), has a top inlet 5 and a bottom outlet 6. The outlet 6 is closed by a frit 8, e.g. of polytetrafluorethylene (PTFE) or similar hydrophobic material, to hold the resin beads and the liquid in the reactor. The frit generally has a pore size between about 1 μm and about 50 μm, preferably between about 5 μm and about 30 μm. Through the tubular shaft 2, the reactor outlet 6 is connected to a drain outlet 7. Draining of liquid from the reactor 1 to the outlet 7 is typically effected by suction, e.g. via a vacuum pump (not shown).

The support 3 is mounted in the system for microwave-assisted solid phase synthesis such that the reactor vial 1 is received in a microwave cavity thereof for microwave heating of the resin beads in the reactor vial.

The mixer motor 4 is controlled by a control unit (not shown) by which desired angular displacements and rotation speeds of the motor can be set. The operation of the mixing apparatus is as follows.

Through control of the control unit, the mixer motor 4 spins the reactor vial 1 about its centre axis in a non-continuous fashion. The spinning reactor vial forces its content of resin and reagents to also start rotating. After a given time, the direction of the rotation of the reactor vial 1 is reversed which forces a turbulence in the resin/reagent mix before it catches up with the reactor vial movement again. This procedure is then repeated. This turbulence caused by the repeated reversal of the rotational direction has a mixing effect.

Compared to the conventional vortex mixing, there are two major benefits of rotation about the central axis in alternating directions, viz. (i) a larger reactor can be used (more efficient use of the microwave cavity volume), and (ii) a greater working volume is permitted (substantially reduced surface turbulence and splashing). Preferably the reactor vial 1 is arranged essentially vertical, preferably also essentially parallel to the rotatable tubular shaft 2, so that the maximum working volume is permitted.

A typical workflow for an amino acid addition cycle in solid phase peptide synthesis is as follows:

Place functionalized resin beads in the reactor (each bead, e.g. of polystyrene, supporting at least one protected amino acid or amino acid sequence) and swell with solvent and mix by actuating the mixer motor (4).

Drain using vacuum via syringe outlet (7).

Deprotect with solvent and mix by actuating the mixer motor (4),

Drain using vacuum via syringe outlet (7).

Couple amino acid during microwave heating and mix by actuating the mixer motor (4).

Drain using vacuum via syringe outlet (7).

Wash with solvent and mix by actuating the mixer motor (4).

Drain using vacuum via syringe outlet (7).

Repeat wash if needed.

The reactor vial may be irradiated with microwaves to heat the reaction mixture at desired synthesis steps and/or during the concentric clockwise and anti-clockwise rotation.

Typical reactor vial (1) volumes are in the range of about 10 to 30 mL.

A typical rotation angle is about 720°, and an exemplary frequency is about 0.5-1 cycles per second.

Optionally, the rotation angle (angular excursion) in the clockwise direction is different from the rotation angle in the anti-clockwise direction.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. An apparatus for microwave assisted solid phase synthesis using solid-phase resin beads mixed with a liquid solvent, comprising:
    a generally cylindrical reactor vial, the reactor vial made of microwave transparent material, the reactor vial having a central axis, the central axis of the reactor vial extending through an interior of the reactor vial, the reactor vial having an inlet and an outlet;
    a porous frit, the porous frit closing the outlet of the reactor vial, the porous frit configured to prevent discharge of the resin beads from the reactor vial, the porous frit configured to drain the solvent from the reactor vial; and
    a mixer motor vertically beneath the reactor vial, such that a central axis of the mixer motor is aligned with the central axis of the reactor vial; and
    a control unit configured to control the mixer motor to rotate the reactor vial concentrically around the central axis of the reactor vial in alternating clockwise and anti-clockwise directions, such that the reactor vial is only rotated around the central axis extending through the interior of the reactor vial and is not shaken.

2. The apparatus according to claim 1, wherein the frit is configured to drain the solvent from the reactor vial, based on a vacuum being applied to the outlet.

3. The apparatus according to claim 1, wherein the frit has a pore size from about 1 to about 50 μm.

4. The apparatus according to claim 3, wherein the frit has a pore size from about 5 to about 30 μm.

5. The apparatus according to claim 1, wherein the frit is made of a hydrophobic material.

6. The apparatus according to claim 5, wherein the frit is made of PTFE.

7. A method for microwave assisted solid phase synthesis, comprising:
    providing an apparatus according to claim 1, wherein the reactor vial contains functionalized resin beads, a solvent and reactants for solid phase synthesis;
    subjecting the reactor vial to microwave heating; and
    mixing the contents of the reactor vial by rotating the reactor vial concentrically around the central axis of the reactor vial in alternating clockwise and anti-clockwise directions, such that the reactor vial is only rotated around the central axis extending through the interior of the reactor vial and is not shaken.

8. The method according to claim 7, wherein,
    the reactants for solid phase synthesis are reactants for solid phase peptide synthesis, and
    the solid phase synthesis is solid phase peptide synthesis.

9. The apparatus according to claim 1, wherein the reactor vial is arranged essentially vertical.

* * * * *